(12) United States Patent
Elkind

(10) Patent No.: US 11,160,244 B2
(45) Date of Patent: Nov. 2, 2021

(54) PEPPER PLANTS PRODUCING FRUITS WITH IMPROVED PROPERTIES

(71) Applicant: Yissum Research Development Company of the Hebrew University of Jerusalem LTD., Jerusalem (IL)

(72) Inventor: Yonatan Elkind, Rehovot (IL)

(73) Assignee: YISSUM RESEARCH DEVELOPMENT COMPANY OF THE HEBREW UNIVERSITY OF JERUSALEM LTD., Jerusalem (IL)

(*) Notice: Subject to any disclaimer, the term of this patent is extended or adjusted under 35 U.S.C. 154(b) by 0 days.

(21) Appl. No.: 15/563,166

(22) PCT Filed: Mar. 31, 2016

(86) PCT No.: PCT/IB2016/051843
§ 371 (c)(1),
(2) Date: Sep. 29, 2017

(87) PCT Pub. No.: WO2016/157123
PCT Pub. Date: Oct. 6, 2016

(65) Prior Publication Data
US 2018/0084748 A1   Mar. 29, 2018

(30) Foreign Application Priority Data
Mar. 31, 2015   (EP) .................................. 15305477

(51) Int. Cl.
| | |
|---|---|
| *A01H 5/08* | (2018.01) |
| *A01H 6/82* | (2018.01) |
| *A01H 5/10* | (2018.01) |
| A01H 1/06 | (2006.01) |
| A01H 4/00 | (2006.01) |
| C12N 15/82 | (2006.01) |

(52) U.S. Cl.
CPC ............... *A01H 6/822* (2018.05); *A01H 5/08* (2013.01); *A01H 5/10* (2013.01); *A01H 1/06* (2013.01); *A01H 4/005* (2013.01); *A01H 4/008* (2013.01); *C12N 15/8261* (2013.01)

(58) Field of Classification Search
None
See application file for complete search history.

(56) References Cited

U.S. PATENT DOCUMENTS 5,945,580 A * 8/1999 Dunsmuir .......... C12N 15/8246
435/320.1

FOREIGN PATENT DOCUMENTS

| | | | | |
|---|---|---|---|---|
| EP | 1553817 | * | 7/2005 | ............... A01H 5/08 |
| EP | 1553817 B1 | * | 1/2009 | ............... A01H 5/08 |
| WO | WO 2005/015984 A1 | | 2/2005 | |
| WO | WO 2010/004583 A2 | | 1/2010 | |

OTHER PUBLICATIONS

Ghosh et al. The N-glycan processing enzymes alpha-mannosidase and beta-D-N-acetylhexosaminidase are involved in ripening-associated softening in the non-climacteric fruits of capsicum. J Exp Bot. Jan. 2011;62(2):571-82. Epub Oct. 28, 2010. (Year: 2011).*
Cherian et al. 'Movers and shakers' in the regulation of fruit ripening: a cross-dissection of climacteric versus non-climacteric fruit. J Exp Bot. Sep. 2014;65(17):4705-22. Epub Jul. 3, 2014. Review. (Year: 2014).*
Ben-Yehoshua et al., "Mode of Action of Plastic Film in Extending Life of Lemon and Bell Pepper Fruits by Alleviation of Water Stress," Plant Physiol., vol. 73, No. 1, 1983 (Dec. 31, 1983), pp. 87-93.
Cheng et al., "Changes in Biochemical Characteristics Related to Firmness during Fruit Development of Pepper (*Capsicum annuum* L.)," Europ.J.Hort.Sci., vol. 73, No. 4S, 2008 (Aug. 2008), pp. 155-161, XP0055212167.
Eggink et al., "A Taste of Sweet Pepper: Volatile and Non-volatile Chemical Composition of Fresh Sweet Pepper (*Capsicum annuum*) in Relation to Sensory Evaluation of Taste," Food Chemistry, vol. 132, No. 1, 2012 (Available online Oct. 31, 2011), pp. 301-310, XP028344725.
Extended European Search Report, dated Sep. 28, 2015, for European Application No. 15305477.0.
International Search Report (form PCT/ISA/210), dated May 24, 2016, for International Application No. PCT/IB2016/051843.
Penchaiya et al., "Non-destructive Measurement of Firmness and Soluble Solids Content in Bell Pepper Using NIR Spectroscopy," Journal of Food Engineering, vol. 94, 2009 (Available online Mar. 28, 2009), pp. 267-273, XP026154856.

* cited by examiner

*Primary Examiner* — Cynthia E Collins
(74) *Attorney, Agent, or Firm* — Birch, Stewart, Kolasch & Birch, LLP

(57) ABSTRACT

The present invention relates to novel plants, in particular to pepper plants capable of producing fruits which can be kept a longer period of time on the plant as well as being stored after harvesting under refrigerated conditions without exhibiting excessive softening. The invention thus refers to pepper plant which produces fruits with significantly increased fruit firmness at the harvesting stage, wherein said increased fruit firmness is controlled by a genetic determinant, monogenic, wherein said increased fruit firmness is defined as a fruit deformation under a 1 kg load force that is lower than that of a fruit from a control pepper plant which does not have the said genetic determinant.

15 Claims, 5 Drawing Sheets

A

B

PEPPER PLANTS PRODUCING FRUITS WITH IMPROVED PROPERTIES

CROSS REFERENCE TO RELATED APPLICATIONS

Figure 1:
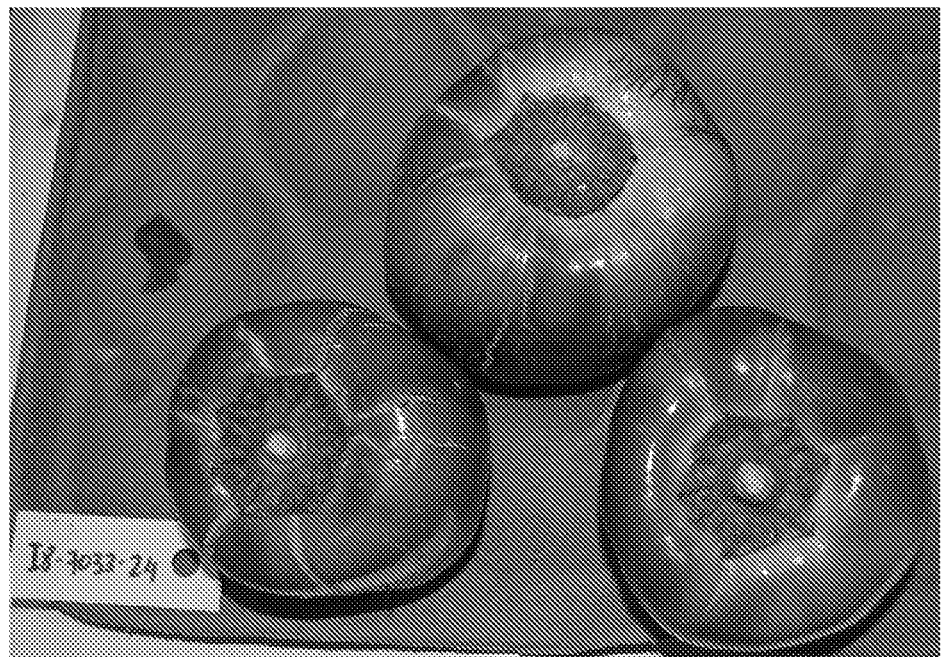
Figure 1:
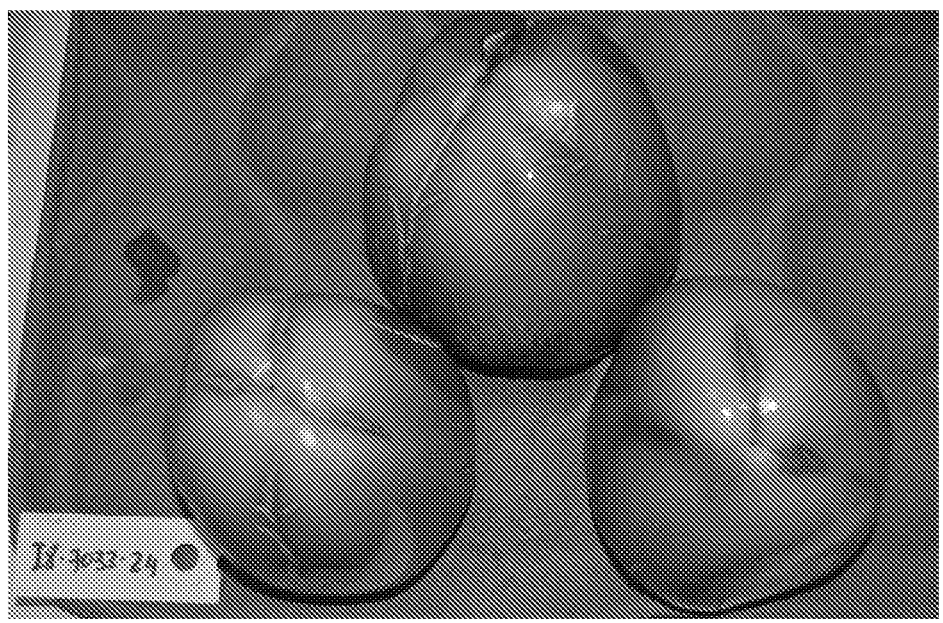

This application is a U.S. National Phase patent application of PCT/IB2016/051843, filed Mar. 31, 2016, which claims priority to European Patent Application No. 15305477.0, filed Mar. 31, 2015, both of which are hereby incorporated by reference in the present disclosure in their entirety.

The present invention relates to novel plants, in particular to pepper plants capable of producing fruits which can be kept a longer period of time on the plant as well as being stored after harvesting under refrigerated conditions without exhibiting excessive softening. The invention also pertains to fruits of said plants as well as to seeds that grow into said plants. The present invention also relates to methods of making and using such plants and their fruits.

Peppers are an important crop worldwide with an estimated cultivation of more than about 30 millions of tons per year for bell peppers fruits. Peppers are Solenaceas from the genus *Capsicum*, which includes the species *Capsicum annuum* and *Capsicum frutescens*. Commercial peppers are diploids with n=12 chromosomes. Peppers are cultivated and used around the world as sweet peppers such as the bell pepper; or as pungent chili peppers, jalapeno peppers, and TABASCO® peppers; or as a source of dried powders of various colors such as paprika.

Peppers represent a valuable source of vitamins and nutrients associated with their pigments and fruit color, including various antioxidants, carotenoids as well as chlorophyll. In the present trend of consumers looking for fresh and healthy vegetables, pepper fruits constitute a product of choice. Peppers fruits are generally green when immature and turn generally red or yellow or orange once ripe.

In some of the markets, peppers are usually harvested green, i.e. at a non-mature stage. Immature pepper fruits generally exhibit a distinct taste and also are less sweet compared to red-mature-fruits.

For all fruit products, fruit firmness which is fit for purpose is essential to meet and possibly exceed consumer expectations. Consumers will reject products with unacceptable fruit firmness, even though other quality attributes such as flavour and colour are good or excellent. Additionally, the supply chain requires an appropriate level of fruit firmness for the effective delivery of high quality fruit to retail outlets. Improving the quality of the raw materials will also encourage the development of healthier diets.

Fruit firmness in pepper is determined by a number of factors. The major factor in most cases is turgor, mainly associated with water content. In some cases cell wall structure, turgor and cuticle properties. Fruit firmness is reported to be a complex trait supposedly depending on the action of many genes. This has made it difficult to dissect the events determining changes in fruit firmness by focusing on changes in cell wall degrading enzymes.

Harvesting pepper fruit when ripening has set in would make maturity determination easier as it would be based on visible peel color and would assure full quality development. After harvest, if no particular humidity and temperature control is put in place, softening advances, increasing the susceptibility of the fruit to handling damage and limiting the marketing period. Slowing down the ripening and softening stages would allow harvesting, transport and storage of partially ripe, or fully ripe, but firm fruits.

Pepper fruits, also commonly referred to as "peppers", are highly perishable. After harvesting, they are prone to water loss, softening and shriveling, which renders them unappealing to customers. Pepper crops produce peaks of fruits that are mature around the same time and have to be harvested quickly to avoid losses. This leads to waves and picks of production, followed by periods of low supply. Furthermore, frequent harvest is not very efficient from an economic point of view and it is more favorable to harvest more fruits in a reduced number of harvests that few fruits in a high number of harvests.

In order to address this problem and bring flexibility in the supply chain, substantial efforts have been made to improve the quality of pepper fruits during post-harvest storage. Treatments involving hot water and polyethylene packing (Gonzalez-Aguilar et al (1999) Journal of Food Quality 22: 287-299), application of $CO_2$ (Wang (1977) J. Amer. Soc. Hort. Sci. 102: 808-812) or other chemicals such as chlorine and Imazalil (Miller et al. (1983) Proc. Fla. State Hort. Soc. 96: 345-350) or chitosan (E I Ghaouth et al. (1991) Journal of Food Processing and Preservation 15: 359-368), have been described. However, these treatments require substantial investments and increase costs of production. Moreover, some of them promote fungal growth or undesired off-flavor production (E I Ghaouth et al. (1991) Journal of Food Processing and Preservation 15: 359-368).

Attempts to increase post-harvest shelf-life of pepper fruits have also been made by genetic engineering approaches. For example, U.S. Pat. No. 5,945,580 reports the transformation of *Capsicum annuum* with DNA sequences of a hemi-cellulase gene. Reduction of hemi-cellulase activity in fruits of transformed plants was measured, leading to a moderate increase in the proportion of acceptable fruits after post-harvest storage at 4 C. However, the commercial viability and public acceptability of genetically modified crops is poor.

An alternative strategy has concentrated on delaying fruit ripening, whereby unripe fruits are usually harvested and let ripen post-harvest. For example, U.S. Pat. No. 4,843,186 discloses peppers comprising the native pepper Rin gene and their delayed ripening.

However, maturation of pepper fruits is a slow process and post-harvest ripening of pepper fruits results in wilted, low-quality fruits.

EP1553817 discloses pepper plant producing fruits with extended storability on the plant as well as after harvesting characterized by the fact that the fruits do not wilt, show 5 of less yellow spot, remain bright and firm for a long period of time. However the fact is that the underlying trait is phenotypically and genetically complex, likely multigenic and consequently difficult to manipulate and to introgress in a broad variety of genetic backgrounds without linkage drag effects. Indeed, fruit quality appears as a quantitative trait involving many genes and yet the identity of the majority of these genes remains obscure.

The formation of the fruit post anthesis is usually following a three steps scheme. First, the fruit reaches the immature green stage wherein the fruit increases its size and weight. Next when it is still green while having reached its fully expanded size it is mature green (at this stage green peppers are usually harvested). This stage is followed by a stage which is called breaker stage corresponding to the period of time when the first sign of coloring of the fruit appears. The breaker stage is followed by the ripe stage where the fruit is fully red, yellow or orange depending of red, yellow or orange genotype, respectively. Usually, fruits for direct marketing are harvested when the colored portion of the fruit reaches more than 90%. In certain cases (very soft or very high price produces) fruits are harvested when 60% is colored and reach their final full color during transportation and storage.

Typically, the firmness of the pepper fruit has the tendency to rapidly decrease once the fruit has reached the ripe stage while this stage corresponds to its maximum in term of taste and nutritional value. The fruits become soft and flabby with unappealing texture or appearance and lose their typical crunchy and juicy texture.

It is thus apparent from the prior art that there is a need to modify pepper fruit firmness and to delay the point of softening in particular so that the ripe fruits stay on the vine for a longer period of time without affecting fruit firmness. The fruits would then keep the same firmness while accumulating more flavour and taste components and thus exhibit a final better taste compared to fruits that have been harvested earlier. Such increased firmness of the fruit would allow a longer period of time for harvesting since the fruits could be left on the vine without the associated softening which would be detrimental for the steps of handling, packing and delivery to the supermarket shelves for example.

There is an unmet need in the pepper trade to reduce peaks in production and to favor a constant supply of fresh, firm and crispy products, while keeping production costs low. There is also an unmet need for improved pepper plants and for alternative and improved storage methods for pepper fruits and to save labor.

The present invention addresses the need for more constant supply of pepper fruits, which keep their organoleptic properties, particularly texture, for an extended period of time, on the vine and/or once harvested when kept refrigerated or not. This would thus provide flexibility in the peppers supply chain.

SUMMARY OF THE INVENTION

An investigation has been conducted from a population of pepper plants wherein a plant producing fruits exhibiting unusual mechanical properties was identified. Indeed, the fruits of said plant were displaying and unusual extra hard texture becoming firmer during time, cracked surface and non-ripening fruit; ie stayed green and did not develop taste or sweetness. This plant was isolated and it was identified that this trait was monogenic and recessive. It is important here to indicate that a trait—referring to a characteristic or phenotype—may be inherited in a dominant or recessive manner, or in a partial or incomplete-dominant manner. A trait may be monogenic (i.e. determined by a single locus) or polygenic (i.e. determined by more than one locus) or may also result from the mutual interaction among genes or interaction of one or more genes with the environment. A dominant trait results in a complete phenotypic manifestation at heterozygous or homozygous state; a recessive trait manifests itself only when present at homozygous state. Upon selfing of the selected plant, seeds failed to germinate. Then, pollen from this selected plant was collected and used for crossing the said plant with normal plants (originating from the same population but without the trait of extra hard texture and non-ripening fruits) which were used as the female parent. Plants derived from second generation of the crossed material (F2) and other consequent generations were segregating populations where seeds were derived from such single plants, the proportion of non-ripening and extra hard fruits was in agreement with 1:3 ratio, indicating a single recessive Mendelian nature for the trait of cracked surface, extra hard texture and non-ripening fruits. Surprisingly, the heterozygous plants for the said trait which were generated did not show drawback of the homozygous plant, (extra hard texture and non-ripening) but did undergo normal coloring and ripening while exhibiting, to a valuable extend, a trait of enhanced firmness at breaker and ripe stage. The advantages and benefits of this trait when present, particularly at heterozygous state, are detailed below.

When the identified trait is homozygous, the fruits are extra-hard, do not ripe and are cracked. However when the trait is heterozygous, the fruits do ripe normally, are not cracked and exhibit an increased firmness all along the ripening process till harvest and even after. The advantage of having an enhanced firmness at the harvesting stage as well as after the stage of usual harvesting, ie ripe and over ripe, allows the fruit to remain firm well after the stage of full ripening.

The inventors noticed that the plants homozygous for trait do contain seeds that fail to germinate and need to undergo embryo rescue in order to generate plant due to lack of endosperm around the embryo.

Then, when pepper plant homozygous for the extra-hard and non-ripening trait are grown, they can be used to be crossed with other pepper plants, particularly sibling pepper plants, which do not contain the said trait. Upon crossing of the said other plant without the trait of the invention, then 100% of the offspring of such cross is heterozygous for the said trait, thus giving normal ripening fruits but with enhanced firmness at the harvesting stage and which keep essentially the same firmness after this stage while the normal fruits (not having the genetic determinant, locus or trait according to the invention) undergo progressive and irremediable softening.

The plants that are heterozygous or homozygous for the trait (or locus) can be used to transfer the genetic determinant for such a trait into different pepper plant genome by any mean known by the man skilled in the art. Preferably, the plants according to the invention, (homozygous or heterozygous for the trait (or locus) of the invention) are used as female when crossed with normal pepper plant not having the said trait or locus. When the trait genetic nature is kept at heterozygous state, the associated phenotype is positive and beneficial for the grower. Since the trait is monogenic, it is easily transferable and the phenotype associated can easily be bestow upon various genetic backgrounds. On the top of that, assuming that the phenotype of interest is attached to the heterozygous state of the trait, the obtention of any pepper plant with the trait at heterozygous state according to the present invention is very easy. Indeed, one single cross of any pepper plant with a heterozygous plant for the trait according to the present invention allows to obtain 50% of the progeny heterozygous for the trait and thus having the phenotype according to the present invention. When the trait/locus is homozygous, the associated phenotype does also present advantageous benefits, for example in the case of specialty products such as industry peppers for which high firmness is a key criteria while the cracking is not a default. Furthermore, some of the drawbacks of the homozygous state of the locus/trait of the invention, such as cracking may be managed thanks to cultivation methods by closer control of day/night temperature shift which is an environmental factor that may triggers or worsen the cracking of fruits.

The inventors have defined that the trait is associated to a genetic determinant, a locus, likely a gene, and is surprisingly associated to significantly increased fruit firmness in pepper at the harvesting stage, when present at heterozygous state. The said trait is controlled by a genetic determinant that is stable and thus can be stably inherited to progeny plants and introgressed into commercial pepper varieties.

The present invention therefore relates in a first aspect to a pepper plant which produces fruits with significantly increased fruit firmness at the harvesting stage, wherein said increased fruit firmness is controlled by a genetic determinant, wherein said increased fruit firmness is defined as a fruit deformation under a 1 kg load force that is lower than that of a fruit from a control pepper plant which does not have the said genetic determinant.

In one embodiment the pepper fruit deformation of a pepper fruit according to the present invention, under a 1 kg force load represents 50% to 95% of that of a fruit from a control pepper plant which does not have the said genetic determinant.

In another embodiment the pepper fruit deformation of a pepper fruit according to the present invention, under a 1 kg force load, represents 50% to 80% of that of a fruit from a control pepper plant which does not have the said genetic determinant.

In a further embodiment the pepper fruit deformation of a pepper fruit according to the present invention, under a 1 kg force load, represents 50% to 70% of that of a fruit from a control pepper plant which does not have the said genetic determinant.

The pepper fruit firmness is measured thanks to the fruit deformation, measured in mm, when the fruit is put under a 1 kg load. The instrument and methodology as described in Example section have been designed according to Ben-Yehoshua, S. et al (Mode of action of plastic film in extending life of lemon and bell pepper fruits by alleviation of water stress. 1983, Plant Physiology 73: 87-93). Fruit firmness was determined with a compression tester using a 1 kg weight. The deformation was measured 10 s after exerting the force on the fruit. The firmer the fruit, the lower were the reading.

There is also provided a method of producing a pepper plant which provides fruit with increased fruit firmness at the harvesting stage as herein described.

There is also provided a method of producing an offspring pepper plant which produces fruits with increased fruit firmness at the harvesting stage comprising the steps of detecting a genetic determinant associated to increased fruit firmness at the harvesting stage in a pepper donor plant, and transferring a nucleic acid comprising such a genetic determinant thus detected to a recipient pepper plant, wherein said increased fruit firmness at the harvesting stage is measured in fruit from an offspring pepper plant compared to fruit from a control pepper plant. The transfer of nucleic acid can be performed by any of several methods known in the art e.g. transformation, by protoplast fusion, by a doubled haploid technique or by embryo rescue or by introgression through crossing.

There is also provided a pepper plant, or part thereof, obtainable by a method as described herein.

There is also provided a cultivated pepper plant comprising a genetic determinant responsible for increased fruit firmness at the harvesting stage as described hereinabove.

There is also provided a hybrid pepper plant, or part thereof, obtainable by crossing a pepper plant as described hereinabove with a pepper plant that exhibits commercially desirable characteristics.

There is also provided pepper seed that growths into a pepper plant as described hereinabove.

There is also provided pepper seed produced by crossing a pepper plant as described hereinabove with a plant having desirable phenotypic traits to obtain a plant that has significantly increased fruit firmness at harvesting stage compared to a control plant. There is also provided the use of a pepper plant according to the present invention for expanding the harvesting slot of pepper fruit and/or for use in the fresh cut market or for food processing.

There is also provided processed food made from a pepper plant comprising the genetic determinant as described herein.

In one embodiment, the present invention provides a pepper plant growing fruit with increased firmness which are edible and of high quality and suitable of being used as fresh produce, as fresh cut produce, or for processing such as, for example, canning.

The pepper plant according to the invention and as described herein before may grow a sweet pepper including a dolce-type pepper, a bell pepper, a big rectangular pepper, a conical pepper, a long conical pepper or a blocky-type pepper. The fruit of said plant at maturity may be an evergreen, a yellow, orange, ivory, brown, purple, or red fruit. The pepper plants according to the present invention are characterized in that the genetic determinant is homozygous.

In another embodiment, the pepper plants according to the present invention are characterized in that the genetic determinant is heterozygous.

The plant according to the invention and as described herein before may be an inbred, a dihaploid or a hybrid and/or a male sterile, with the provision that the genetic determinant of the invention is homozygous or heterozygous, particularly heterozygous. In the context of an inbred, this means that the said inbred is homozygous for all locus except the locus associated with the trait of the invention, increased fruit firmness, but homozygous for the rest of the loci.

In one embodiment, the pepper plant according to the invention and as described herein before contains a "increased fruit firmness" trait governed by a genetic determinant, which is obtainable from a hybrid pepper *Capsicum annuum* A13-1517-6 deposited with NCIMB, Aberdeen AB21 9YA, Scotland, UK on Feb. 5, 2015 under accession number NCIMB 42356. Those hybrid peppers plants are heterozygous for the genetic determinant according to the present invention and can be used for bestowing the trait/locus according to the present invention upon any other pepper plant. Preferably, the deposited plant is used as female plant when crossed with another pepper plant that does not contain the trait/locus/genetic determinant according to the present invention.

In the context of the present invention, the terms trait or locus or genetic determinant are used in order to refer to the genetic element which is monogenic as demonstrated herein and is directing the phenotype of the pepper plants according to the present invention, i.e. increased fruit firmness.

In preferred embodiment, the genetic determinant of the pepper plant according to the present invention is monogenic.

In one embodiment of the invention, the "increased fruit firmness" trait (or locus or genetic determinant) or a plant comprising said trait is obtainable from any of the hybrid plants grown from the deposited seeds by growing the F2 progeny of said hybrid. In particular, the "increase firm firmness" trait or a plant comprising said trait is obtainable from any of the deposited hybrid plants by i) germinating seed of said plants and growing a mature, fertile plant therefrom; ii) inducing self-pollination of said plant grown under (i), growing fruits and harvesting the fertile seeds therefrom, and iii) growing plants from the seeds harvested under ii) and selecting plants which grow fruits with increased fruit firmness.

In one embodiment, the invention relates to plant material obtainable from a plant according to the invention and as described herein before including, but without being limited thereto, leaves, stems, roots, flowers or flower parts, fruits, pollen, egg cells, zygotes, seeds, cuttings, cell or tissue cultures, or any other part or product of the plant which still exhibits the increased fruit firmness phenotype according to the invention, particularly when grown into a plant that produces fruits.

The invention further relates to an agronomic method of producing pepper plant producing pepper fruits with increased fruit firmness comprising the steps of:
i) providing a pepper plant according to the invention and as characterized herein before;
ii) multiplicating/propagating said pepper plant
iii) allowing the plant to grow pepper fruits with increased fruit firmness; and
iv) harvesting said pepper fruits.

In one embodiment of the invention, the multiplication or propagation of the pepper plant is done either through seeds or by vegetative propagation.

The invention further relates to a method of producing a pepper plant producing fruits with increased fruit firmness comprising the steps of
i) providing seeds of an F1 hybrid pepper plant according to the present invention;
ii) germinating said seed and growing a mature, fertile plant therefrom;
iii) inducing self-pollination of said plant grown under (ii), growing fruits and harvesting the fertile seeds therefrom, and
iv) growing plants from the seeds harvested under iii) and selecting plants which grow fruits with increased firm firmness.

Due to the heterozygous nature of the trait of increased fruit firmness and the monogenic nature of the trait of F1 hybrid pepper plants used in i) such as the ones deposited under NCIMB 42356, the segregation observed in plants obtained in step iv) above is: 50% of plants according to the present invention, ie increased fruit firmness with normal ripening fruits and non-cracked fruits (heterozygous for the genetic determinant of the trait); 25% of plants that are normal plants with normal ripening fruits and non-cracked fruits but without increased fruits firmness and 25% of plants are plants with non-ripening, heavily cracked, and extra hard texture fruits (homozygous for the genetic determinant of the trait).

In one embodiment, the F1 hybrid seed used in said method according to the invention is the hybrid seed, which is obtainable from a hybrid pepper plant selected from the group of hybrids consisting of *Capsicum annuum* A13-1517-6 grown from seeds deposited with NCIMB, Aberdeen AB21 9YA, Scotland, UK on Feb. 5, 2015 under accession number NCIMB 42356.

This plant is heterozygous for the trait/locus of the invention, and allows upon selfing to obtain offsprings that segregate for the trait of the invention.

The invention further relates to a method of producing a pepper plant producing fruits with increased fruit firmness comprising the steps of
i) providing seeds of an F1 hybrid pepper plant according to the present invention;
ii) germinating said seed and growing a mature, fertile plant therefrom;
iii) crossing the plant obtained in ii) with a pepper plant which does not have the trait of increased fruit firmness, growing fruits and harvesting the fertile seeds therefrom and
iv) growing plants from the seeds harvested under iii) and selecting plants which grow fruits with increased firm firmness.

Due to the heterozygous nature of the trait of fruit having normal ripening and increased fruit firmness and the monogenic nature of the trait, the segregation observed in plants obtained in step v) above is: 50% of plants according to one embodiment of the present invention, ie increased fruit firmness with normal ripening fruits and non-cracked fruits (heterozygous for the genetic determinant of the trait); 50% of plants that are normal plants with normal ripening fruits and non-cracked fruits but without increased fruits firmness.

In one embodiment, the F1 hybrid seed used in said method according to the invention is the hybrid seed, which is obtainable from a hybrid pepper plant selected from the group of hybrids consisting of *Capsicum annuum* A13-1517-6.grown from seeds deposited with NCIMB, Aberdeen AB21 9YA, Scotland, UK on Feb. 5, 2015 under accession number NCIMB 42356.

In one embodiment, the pepper plant which does not have the trait of increased fruit firmness which is crossed in step iii) can be any pepper plant variety.

The selected pepper plants in step iv) are heterozygous for the genetic determinant of the trait according to the present invention and can be used for further back-crosses with the second pepper parent plant which does not contain the genetic determinant of increased fruit firmness in order to convert that initial pepper plant into a very same one with the difference of having in its genome the genetic determinant of increased fruit firmness. For each generation 50% of the plants will be heterozygous for the genetic determinant and will exhibit the trait of increased fruit firmness according to the present invention.

Accordingly it is possible to convert any pepper plant into a pepper plant according to the present invention by sexual crossing of such any pepper plant with a pepper plant according to the present invention, i.e. that contains the genetic determinant in heterozygous state. Preferably the female plant used in the cross is plant according to the invention in order to obtain plant, in the first generation that exhibit the phenotype of enhanced fruit firmness. The genetic determinant for the trait of the present invention is obtainable from a hybrid pepper plant selected from the group of hybrids consisting of *Capsicum annuum* A13-1517-6 grown from seeds deposited with NCIMB, Aberdeen AB21 9YA, Scotland, UK on Feb. 5, 2015 under accession number NCIMB 42356.

In order to do so, the deposited plant may be used as a female parent since the maternal genotype will govern the first generation phenotype of the fruit.

If one uses, the deposited hybrid plant as male parent, i.e. a pollen donor, to be crossed with a normal pepper plant as female that does not contain the locus/trait according to the invention, then the first generation progeny will not exhibit the enhanced fruit firmess since the maternal tissue of the ovary gives rise to the pericarp of the fruit. In such a situation, the first generation progeny has to undergo self-pollination and this will give 25% of homozygous and 75% of heterozygous (for the trait/locus of the invention) plants. Those plants will exhibit the phenotype of enhanced fruit firmess.

Such genetic determinant is inheritable and can be transmitted thru generation by techniques known to the man skilled in the art of plant breeding or plant biotechnology.

PLANT BREEDING

The purpose of breeding programs in agriculture and horticulture is to enhance the performance of plants by improving their genetic composition. In essence, this improvement accrues by increasing the frequency of the most favorable alleles for the genes influencing the performance characteristics of interest.

Wild plants provide a rich resource of genetic and phenotypic variation. Traditionally, agricultural or horticultural practice makes use of this variation by selecting a wild plant line or its offspring for having desired genotypic or potential phenotypic properties, crossing it with a line having additional desired genotypic or potential phenotypic properties and selecting from among the offspring plants those that exhibit the desired genotypic or potential phenotypic properties (or an increased frequency thereof).

A growing understanding and utilization of the laws of Mendelian inheritance has in the past century facilitated this selection process. For example, methods for selecting plants, improved with the use of molecular genetic tools recently introduced, for having desired genotypic or potential phenotypic properties have become available based on testing the plant for the presence of a quantitative trait locus (QTL); i.e. for the presence of a genetic determinant containing allele or alleles associated to the expression of a continuously distributed (quantitative) phenotypic trait. Usually a QTL is characterized by one or more markers that statistically associate to the quantitative variation in the phenotypic trait and is essentially synonymous to a gene.

Knowledge of the inheritance of various traits would allow for the selection of lines homozygous or heterozygous for a genetic determinant, QTL, gene, or allele associated to increased fruit firmness. Use of the knowledge of the genetic origin and location of a desired trait or allele in a breeding program can increase the accuracy of the predicted breeding outcome and can enhance the rate of selection compared to conventional breeding programs. For instance, the fact that the genetic basis of a desired trait is heritably associated to another trait can help to increase uniformity for those two traits among the offspring since a parent homozygous for the desired alleles will pass them to most if not all offspring, resulting in a reduced segregation in the offspring.

The presently disclosed subject matter relates to methods of plant breeding and to methods to select pepper plants, particularly cultivated pepper plants as breeder plants for use in breeding programs or cultivated pepper plants having desired genotypic or potential phenotypic properties, in particular those which produce pepper fruit with increased fruit firmness at the harvesting stage.

Accordingly, there is provided a pepper fruit with increased fruit firmness at the harvesting stage associated to a genetic determinant in the pepper plant producing said pepper fruit, wherein said increased fruit firmness is defined as a fruit deformation under a 1 kg load force that is lower than that of a fruit from a control pepper plant which does not have the said genetic determinant.

In one embodiment the pepper fruit deformation of a pepper fruit according to the present invention, under a 1 kg force load represents 50% to 95% of that of a fruit from a control pepper plant which does not have the said genetic determinant.

In another embodiment the pepper fruit deformation of a pepper fruit according to the present invention, under a 1 kg force load, represents 50% to 80% of that of a fruit from a control pepper plant which does not have the said genetic determinant.

In a further embodiment the pepper fruit deformation of a pepper fruit according to the present invention, under a 1 kg force load, represents 50% to 70% of that of a fruit from a control pepper plant which does not have the said genetic determinant.

In a particular embodiment, the harvesting stage is preferably the ripe stage. Alternatively, the harvesting stage can be any chosen point in the development of the pepper fruit, which includes but is not limited to the immature green stage, rapid expansion stage, mature green stage, breaker stage or red ripe stage or 1, 2, 3, 4, 5, 6, 7, 8, 9 or 10 days after any of these stages. In one embodiment, the harvesting stage is the breaker stage plus 7 days.

The trait according to the present invention provides enhanced firmness to pepper fruits at the harvesting stage. The extend of difference regarding the firmness between a pepper fruit according to the present invention (homozygous or heterozygous) and a control pepper plant that does not contain the genetic determinant is obviously dependent of the maturity stage of the fruit. Indeed, before and till the immature green stage, the firmness of a pepper according to the present invention is slightly higher compared to a control pepper. However, the more the fruit become ripe, moving from immature green stage to breaker stage then to ripe, particularly red-ripe, then over ripe, the more the difference in term of firmness become evident. The control pepper fruit, as from immature green stage, shows an evolution of the firmness which is stable and then exhibits a strong decrease of such firmness till and after having reached the ripe stage. On the contrary, the pepper fruit according to the present invention is able to maintain the firmness to a substantially constant level from the immature green stage till the over-ripe stage. In term of fruit deformation under load, the fruit of the pepper plant according to the present invention does not show any substantial increase of the deformation from immature green stage to over-ripe stage, thru mature green, breaker and ripe stages. On the contrary, the control pepper plant exhibit an increase in the deformation as of mature green stage, which even dramatically increase at the ripe stage and even more at the over ripe stage, stage at which the fruit is completely softened and deformed by the load.

In a specific embodiment there is provided a pepper plant producing pepper fruits with increased fruit firmness at the mature green stage associated to at least one genetic determinant in the pepper plant producing said pepper fruit, wherein said firmness wherein said increased fruit firmness is defined as a fruit deformation under a 1 kg load force that is lower than that of a fruit from a control pepper plant which does not have the said genetic determinant.

In a specific embodiment there is provided a pepper plant producing pepper fruits with increased fruit firmness at the mature green stage associated to at least one genetic determinant in the pepper plant producing said pepper fruit, wherein said firmness wherein said increased fruit firmness is defined as a fruit deformation under a 1 kg load force that is lower than that of a fruit from a control pepper plant which does not have the said genetic determinant.

In one embodiment, the genetic determinant of the plant according to the invention is homozygous. In another embodiment, the genetic determinant of the plant according to the invention is heterozygous.

In a specific embodiment there is provided a pepper plant producing pepper fruits with increased fruit firmness at the breaker stage associated to at least one genetic determinant in the pepper plant producing said pepper fruit, wherein said firmness wherein said increased fruit firmness is defined as a fruit deformation under a 1 kg load force that is lower than that of a fruit from a control pepper plant which does not have the said genetic determinant.

In a specific embodiment there is provided a pepper plant producing pepper fruits with increased fruit firmness at the ripe stage associated to at least one genetic determinant in the pepper plant producing said pepper fruit, wherein said firmness wherein said increased fruit firmness is defined as a fruit deformation under a 1 kg load force that is lower than that of a fruit from a control pepper plant which does not have the said genetic determinant.

In one embodiment, the genetic determinant of the plant according to the invention is homozygous. In another embodiment, the genetic determinant of the plant according to the invention is heterozygous.

In a specific embodiment there is provided a pepper plant producing pepper fruits with increased fruit firmness at the over ripe stage associated to at least one genetic determinant in the pepper plant producing said pepper fruit, wherein said firmness wherein said increased fruit firmness is defined as a fruit deformation under a 1 kg load force that is lower than that of a fruit from a control pepper plant which does not have the said genetic determinant.

The over ripe stage corresponds to a stage of ripe plus 1 day, ripe plus 2 days, ripe plus 3 days, ripe plus 4 days, ripe plus 5 days, ripe plus 6 days, ripe plus 7 days or ripe plus 8 days.

In one embodiment, the genetic determinant of the plant according to the invention is homozygous. In another embodiment, the genetic determinant of the plant according to the invention is heterozygous.

In one embodiment the increased fruit firmness of the pepper fruit corresponds to deformation of the pepper fruit according to the present invention, under a 1 kg force load which represents 50% to 95% of that of a fruit from a control pepper plant which does not have the said genetic determinant.

In another embodiment the pepper fruit deformation of a pepper fruit according to the present invention, under a 1 kg force load, represents 50% to 80% of that of a fruit from a control pepper plant which does not have the said genetic determinant.

In one embodiment the increased fruit firmness of the pepper fruit corresponds to deformation of the pepper fruit according to the present invention, under a 1 kg force load which, represents 50% to 70% of that of a fruit from a control pepper plant which does not have the said genetic determinant.

In a specific embodiment, there is provided a pepper plant producing pepper fruits with increased fruit firmness at the breaker stage plus 7 days caused by a genetic determinant in the pepper plant producing said pepper fruit, wherein said increased fruit firmness is defined as a fruit deformation under a 1 kg load force that is lower than that of a fruit from a control pepper plant which does not have the said genetic determinant.

In one embodiment the increased fruit firmness of the pepper fruit corresponds to deformation of the pepper fruit according to the present invention, under a 1 kg force load which, represents 50% to 95% of that of a fruit from a control pepper plant which does not have the said genetic determinant.

In one embodiment the increased fruit firmness of the pepper fruit corresponds to deformation of the pepper fruit according to the present invention, under a 1 kg force load which, represents 50% to 80% of that of a fruit from a control pepper plant which does not have the said genetic determinant.

In one embodiment the increased fruit firmness of the pepper fruit corresponds to deformation of the pepper fruit according to the present invention, under a 1 kg force load which, represents 50% to 70% of that of a fruit from a control pepper plant which does not have the said genetic determinant.

In one embodiment, the genetic determinant of the plant according to the invention is homozygous. In another embodiment, the genetic determinant of the plant according to the invention is heterozygous.

The control plant can be any pepper plant which differs from its offspring essentially due to the absence of the genetic determinant, responsible for increased fruit firmness in the pepper plant. The control pepper plant may be selected from any plant, line or population formerly known under the genus name *Capsicum annuum*.

Preferably the genetic determinant responsible for significantly increased pepper fruit firmness of the present invention is a locus identical to the one present in pepper plant *Capsicum annuum* A13-1517-6 grown from seeds deposited with NCIMB, Aberdeen AB21 9YA, Scotland, UK on Feb. 5, 2015 under accession number NCIMB 42356.

In a preferred embodiment the genetic determinant responsible for increased pepper fruit firmness according to the present invention is a locus that is present in the genome of the plant in the homozygous state.

In a preferred embodiment the genetic determinant responsible for increased pepper fruit firmness according to the present invention is a locus that is present in the genome of the plant in the heterozygous state.

In a preferred embodiment, the genetic determinant responsible for increased pepper fruit firmness is a locus as present in heterozygous state in pepper plant *Capsicum annuum* A13-1517-6 grown from seeds deposited with NCIMB, Aberdeen AB21 9YA, Scotland, UK on Feb. 5, 2015 under accession number NCIMB 42356.

In a further aspect, there is provided a pepper plant which produces pepper fruits wherein said plant comprises a genetic determinant, which has similar or identical genetic constitution to the corresponding genetic determinant present in pepper plant *Capsicum annuum* A13-1517-6 grown from seeds deposited with NCIMB, Aberdeen AB21 9YA, Scotland, UK on Feb. 5, 2015 under accession number NCIMB 42356.

PRODUCTION OF PEPPER PLANTS WITH INCREASED FRUIT FIRMNESS BY NON TRANSGENIC METHODS

In some embodiments for producing a pepper plant with increased fruit firmness, protoplast fusion can be used for the transfer of nucleic acids from a donor plant to a recipient plant. Protoplast fusion is an induced or spontaneous union, such as a somatic hybridization, between two or more protoplasts (the cell walls of which are removed by enzymatic treatment) to produce a single bi- or multi-nucleate cell. The fused cell, which can even be obtained with plant species that cannot be interbred in nature, is tissue cultured into a hybrid plant exhibiting the desirable combination of traits. More specifically, a first protoplast can be obtained from a pepper plant or other plant line that contains genetic determinant responsible for increased fruit firmness according to the present invention. A second protoplast can be obtained from a second pepper plant or other plant variety, preferably a pepper plant line that comprises commercially valuable characteristics. The protoplasts are then fused using traditional protoplast fusion procedures, which are known in the art.

Alternatively, embryo rescue can be employed in the transfer of a nucleic acid comprising a genetic determinant as described herein responsible for increased fruit firmness, from a donor pepper plant to a recipient pepper plant. Embryo rescue can be used as a procedure to isolate embryos from plants that fail to produce viable seed. In this process, the fertilized ovary or immature seed of a plant is tissue cultured to create new plants (Pierik, 1999). The presently disclosed subject matter also relates to methods for producing pepper plant with increased fruit firmness comprising performing a method for detecting the presence of a genetic determinant associated to increased fruit firmness in a donor pepper plant as described herein, and transferring a nucleic acid sequence comprising the genetic determinant thus detected, or an increased fruit firmness-conferring part thereof, from the donor plant to a recipient pepper plant. The transfer of the nucleic acid sequence can be performed by any of the methods previously described herein.

An exemplary embodiment of such a method comprises the transfer by introgression of the genetic determinant responsible for increased firm firmness, or nucleic acid sequence containing such genetic determinant, from a donor pepper plant into a recipient pepper plant by crossing the plants. This transfer can thus suitably be accomplished by using traditional breeding techniques. Genetic determinant is introgressed in some embodiments into commercial pepper varieties using marker-assisted selection (MAS) or marker-assisted breeding (MAB). MAS and MAB involves the use of one or more of the molecular markers for the identification and selection of those offspring plants that contain the genetic determinant that is associated with the desired trait. In the context of the presently disclosed subject matter, such identification and selection is based on selection of genetic determinant of the presently disclosed subject matter or markers associated therewith. MAS can also be used to develop near-isogenic lines (NIL) harboring the genetic determinant of interest. Pepper plants developed according to these embodiments can advantageously derive a majority of their traits from the recipient plant, and derive increased fruit firmness from the donor plant. As discussed hereinabove, traditional breeding techniques can be used to introgress a genetic determinant responsible for increased fruit firmness into a recipient pepper plant. In some embodiments, a donor pepper plant that exhibits increased fruit firmness and comprises a genetic determinant encoding for increased fruit firmness is crossed with a recipient pepper plant that in some embodiments exhibits commercially desirable characteristics.

The resulting plant population (representing the F1 hybrids) is then self-pollinated and set seeds (F2 seeds). The F2 plants grown from the F2 seeds are then screened for increased fruit firmness by methods known to the skilled person such as the one described in the Example section.

The selection in the progeny may also be done thanks to the use of a tester plant which is heterozygous for the trait according to the present invention. Assuming that the genotype associated with the phenotype of the plant according to the present invention is a single heterozygous or homozygous genetic determinant, the cross of the plant of the progeny to be tested with a tester plant which is heterozygous or homozygous for the genetic determinant supporting the trait of the present invention will easily be analyzed according to Mendelian inheritance. Thus, depending on the ratio of plant with the trait in the progeny of a cross of the plant to be tested with the tester plant, then the man skilled in the art can determine which plant contain the genetic determinant, according to the present invention, in the heterozygous or homozygous state and thus exhibits the trait of increased firmness at harvesting stage. A tester plant can be the pepper plant *Capsicum annuum* A13-1517-6.grown from seeds deposited with NCIMB, Aberdeen AB21 9YA, Scotland, UK on Feb. 5, 2015 under accession number NCIMB 42356

Pepper plant lines with increased fruit firmness can be developed using the techniques of recurrent selection and backcrossing, selfing, and/or dihaploids, or any other technique used to make parental lines. In a method of recurrent selection and backcrossing, increased fruit firmness trait, ie the genetic determinant for the trait, can be introgressed into a target recipient plant (the recurrent parent) by crossing the recurrent parent with a first donor plant, which differs from the recurrent parent and is referred to herein as the "non-recurrent parent". The recurrent parent is a plant that does not have increased fruit firmness but does possess commercially desirable characteristics. The donor plant may advantageously be the pepper plant *Capsicum annuum* A13-1517-6.grown from seeds deposited with NCIMB, Aberdeen AB21 9YA, Scotland, UK on Feb. 5, 2015 under accession number NCIMB 42356.

In some embodiments, the non-recurrent parent exhibits increased fruit firmness and comprises a nucleic acid sequence that comprise the genetic determinant, that encodes for increased fruit firmness. The non-recurrent parent can be any plant variety or inbred line that is cross-fertile with the recurrent parent.

In one preferred embodiment, the genetic determinant is present in heterozygous state in the recipient plant. In a preferred embodiment, this recipient plant is a female plant.

The present invention is thus directed to the use of a genetic determinant, to confer increased fruit firmness at harvesting stage to a pepper plant lacking said genetic determinant, wherein said genetic determinant is obtainable from pepper plant *Capsicum annuum* A13-1517-6.grown from seeds deposited with NCIMB, Aberdeen AB21 9YA, Scotland, UK on Feb. 5, 2015 under accession number NCIMB 42356.

The man skilled in the art can easily implement the invention in any pepper plant and the information and tool herein provided allow this implementation of the invention. The deposited pepper plant does contain the genetic determinant, in the heterozygous state, of the present invention. Any of the deposited plants can be used by the man skilled in the art as a source for the genetic determinant, associated with increased fruit firmness at harvesting stage.

Further, based on the monogenic character of the trait of the present invention, the man skilled in the art can easily follow the presence of the genetic determinant underlying the trait thru the progeny, crosses and backcrosses thanks to the use of the pepper plant *Capsicum annuum* A13-1517-6.grown from seeds deposited with NCIMB, Aberdeen AB21 9YA, Scotland, UK on Feb. 5, 2015 under accession number NCIMB 42356, as a tester plant or by simply examining the phenotype.

The progeny resulting from a cross between the recurrent parent and non-recurrent parent are backcrossed to the recurrent parent. The resulting plant population can then be screened for increased fruit firmness.

Following screening, the F1 hybrid plants that exhibit an increased fruit firmness phenotype or, in some embodiments, genotype and thus comprise the requisite genetic determinant, responsible for increased fruit firmness, are then selected and backcrossed to the recurrent parent for a number of generations in order to allow for the pepper plant to become increasingly inbred. This process can be performed for two, three, four, five, six, seven, eight, or more generations. In principle, the progeny resulting from the process of crossing the recurrent parent with the increased fruit firmness non-recurrent parent are heterozygous for the genetic determinant, that is responsible for increased fruit firmness according to the present invention.

In a specific embodiment there is provided a method of producing a pepper fruit by growing a pepper plant according to the present invention which provides fruit with increased fruit firmness at harvesting stage as herein described, letting the plant to set fruit and harvesting fruits, wherein said increased fruit firmness is defined as a fruit deformation under a 1 kg load force that is lower than that of a fruit from a control pepper plant which does not have the said genetic determinant.

In one embodiment the pepper fruit deformation of a pepper fruit according to the present invention, under a 1 kg force load represents 50% to 95% of that of a fruit from a control pepper plant which does not have the said genetic determinant.

In another embodiment the pepper fruit deformation of a pepper fruit according to the present invention, under a 1 kg force load, represents 50% to 80% of that of a fruit from a control pepper plant which does not have the said genetic determinant.

In a further embodiment the pepper fruit deformation of a pepper fruit according to the present invention, under a 1 kg force load, represents 50% to 70% of that of a fruit from a control pepper plant which does not have the said genetic determinant.

Alternatively, the harvesting stage can be the immature green stage, rapid expansion stage, breaker stage or red ripe stage or 1, 2, 3, 4, 5, 6, 7, 8, 9 or 10 days after any of these stages.

In a specific embodiment there is provided a method of producing a pepper plant which provides fruit with increased fruit firmness as herein described, wherein the fruit firmness range remains up until breaker stage plus 7 days.

In a further aspect there is provided use of a pepper plant having increased fruit firmness as herein described for expanding the harvesting slot of pepper fruit. The harvesting slot can be expanded by any one of 1, 2, 3, 4, 5, 6, 7, 8, 9 or 10 days.

In a further aspect there is provided use of a pepper plant having increased fruit firmness as herein

DEPOSIT

The following seed sample(s) of pepper plant seeds of *Capsicum annuum* A13-1517-6 were deposited with NCIMB, Ferguson Building, Craibstone Estate, Bucksbum, Aberdeen AB21 9YA, Scotland, UK, on Feb. 5, 2015; under the provisions of the Budapest Treaty in the name of "Yissum the Research Development Company of The Hebrew University of Jerusalem", deposit number(s) NCIMB 42356.

Fruits resulting from reciprocal crosses between normal and plants according to the invention homozygous for the trait of the invention, were examined. In both cases, when plants according to the invention homozygous for the trait of the invention were use as female parents (genotype rr homozygous for the trait/locus according to the present invention) were pollinated with either plants according to the invention homozygous for the trait of the invention (rr) or normal (RR, not carrying the trait/locus according to the present invention) pollen, the phenotypes of the fruits (rR or rr; i.e. heterozygous or homozygous for the trait/locus of the present invention) and seeds which developed were identical to the plants according to the invention homozygous for the trait of the invention, (firm fruits, large seeds, developmentally delayed embryos and lack of an endosperm). When normal female parents (RR, not carrying the trait/locus according to the present invention) were fertilized with either plants according to the invention homozygous for the trait of the invention (rr) or normal pollen (RR), the phenotype of the fruits and seeds appeared normal. However, the heterozygous plants (Rr) were exhibiting a fruit phenotype with enhanced firmness and capable of normal ripening as compared to the normal (RR) plants not carrying the locus of the invention. Such plants are still with the scope of the invention. The results show that the phenotypes of the fruits and seeds of first generation crosses are determined by the genotype of the maternal plant. However, the selfing of this progeny can give rise to plants having fruit with phenotype according to the invention, either homozygous or heterozygous.

If a crossed is achieved using a plant according to the present invention as male, either homozygous or heterozygous, (such as the deposited hybrid pepper plant), and a normal pepper plant as a female, the progeny of the first filial generation will be heterozygous for the trait/locus. This progeny population can thus be self-pollinated and will give rise to a F2 population which will be 33% heterozygous or homozygous for the trait/locus according to the invention and will exhibit the phenotype of enhanced fruit firmness.

Plants of the present invention are particularly advantageous in that they allow for a longer harvest period and for a lower harvest frequency of the crop, while maintaining high fruit quality and avoiding losses. Mature fruits can be kept on the plant and the harvest of fruits grown from plants of the present invention can be delayed by several weeks. Thus, the present invention offers the possibility for the grower to harvest less often a higher fruit quantity per plant. A better planning of the harvest, better efficiency of the harvest and more ripe fruits per harvest is reached while keeping the same fruit quality. The present invention also allows for better planning of labor for harvest, grading and packing of the product, and for better planning for sales and delivery of the product, thereby substantially reducing losses in the business chains and thus production costs.

DEFINITIONS

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

As used herein, the term "about" when referring to a value or to an amount of mass, weight, time, volume, concentration or percentage is meant to encompass variations of in some embodiments +−20%, in some embodiments +−40%, in some embodiments +−5%, in some embodiments +−4%, in some embodiments +−0.5%, and in some embodiments +−0.1% from the specified amount, as such variations are appropriate to perform the disclosed method.

An "allele" is understood within the scope of the invention to refer to alternative or variant forms of various genetic units identical or associated to different forms of a gene or of any kind of identifiable genetic determinant, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, chemical or structural modification, transcription regulation or post-translational modification/regulation. In a diploid cell or organism, the two alleles of a given gene or genetic determinant typically occupy corresponding loci on a pair of homologous chromosomes.

An allele associated to a quantitative trait may comprise alternative or variant forms of various genetic units including those that are identical or associated to a single gene or multiple genes or their products or even a gene disrupting or controlled by a genetic factor contributing to the phenotype represented by said QTL.

As used herein, the term "backcross", and grammatical variants thereof, refers to a process in which a breeder crosses a hybrid progeny back to one of the parents, for example, a first generation hybrid F1 with one of the parental genotypes of the F1 hybrid. In some embodiments, a backcross is performed repeatedly, with a progeny individual of one backcross being itself backcrossed to the same parental genotype.

As used herein, the term "breeding", and grammatical variants thereof, refer to any process that generates a progeny individual. Breeding can be sexual or asexual, or any combination thereof. Exemplary non-limiting types of breeding include crossings, selfings, doubled haploid derivative generation, and combinations thereof.

For the purpose of the present invention, the term "co-segregation" refers to the fact that the allele for the trait and the allele(s) for the markers) tend to be transmitted together because they are physically close together on the same chromosome (reduced recombination between them because of their physical proximity) resulting in a non-random association of their alleles. "Co-segregation" also refers to the presence of two or more traits within a single plant of which at least one is known to be genetic and which cannot be readily explained by chance.

A "cultivated pepper plant" or "cultivated pepper" is understood within the scope of the invention to refer to a plant that is no longer in the natural state but has been developed by human care and for human use and/or growing purposes and/or consumption. "Cultivated pepper plants" are further understood to exclude those wild-type species which comprise the trait being subject of this invention as a natural trait and/or part of their natural genetics.

As used herein, the term "dihaploid line", refers to stable inbred lines issued from another culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially not segregating anymore (stable).

As used herein, the term "gene" refers to a hereditary unit including a sequence of DNA that occupies a specific location on a chromosome and that contains the genetic instruction for a particular characteristic or trait in an organism.

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are associated or unassociated. In some embodiments, an individual's genotype relates to one or more genes that are related in that the one or more of the genes are involved in the expression of a phenotype of interest (e.g. a quantitative trait as defined herein). Thus, in some embodiments a genotype comprises a summary of one or more alleles present within an individual at one or more genetic loci of a quantitative trait. In some embodiments, a genotype is expressed in terms of a haplotype. "Heterozygous" is understood within the scope of the invention to refer to dissimilar alleles at one or more corresponding loci on homologous chromosomes.

"Homozygous" is understood within the scope of the invention to refer to similar alleles at one or more corresponding loci on homologous chromosomes.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the phrase "inbred line" refers to a genetically homozygous or nearly homozygous population. An inbred line, for example, can be derived through several cycles of brother/sister breedings or of selfing or in dihaploid production. In some embodiments, inbred lines breed true for one or more phenotypic traits of interest. An "inbred", "inbred individual", or "inbred progeny" is an individual sampled from an inbred line.

As used herein, the terms "introgression", "introgressed" and "introgressing" refer to the process whereby one gene or a plurality of genes, a QTL or haplotype of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

"Locus" is understood within the scope of the invention to refer to a region on a chromosome, which comprises a gene or any other genetic determinant or factor contributing to a trait.

As used herein, the term "offspring" plant refers to any plant resulting as progeny from a vegetative or sexual reproduction from one or more parent plants or descendants thereof. For instance an offspring plant can be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings of F1s, F2s and the like. An F1 can thus be (and in some embodiments is) a hybrid resulting from a cross between two true breeding parents (true-breeding is homozygous for a trait), while an F2 can be (and in some embodiments is) an offspring resulting from self-pollination of the F1 hybrids.

As used herein, the expression "trait" refers to a characteristic or phenotype, e.g., mature fruit color or a disease or pathogen resistance. A trait may be inherited in a dominant or recessive manner, or in a partial or incomplete-dominant manner. A trait may be monogenic (i.e. determined by a single locus) or polygenic (i.e. determined by more than one locus) or may also result from the mutual interaction among genes or interaction of one or more genes with the environment.

As used herein, the expression "phenotype" or "phenotypic trait" refers to the appearance or other detectable characteristic of an individual, resulting from the interaction of its genome, proteome and/or metabolome with the environment.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

In the context of the present invention, the expression "a seed of a plant according to the present invention" or "a seed of a pepper plant according to the present invention" does refer to a seed capable to grow into a plant according to the present invention and not necessarily a seed of a plant of the present invention.

As used herein, the phrase "plant part" refers to a part of a plant, including single cells and cell tissues such as plant cells that are intact in plants, cell clumps, and tissue cultures. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calii, and the like.

"Plant tissue" as used herein means a group of plant cells organized into a structural and functional unit. Any tissue of a plant in a plant or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

"Polymorphism" is understood within the scope of the invention to refer to the presence in a population of two or more different forms of a gene, genetic marker, or inherited trait or a gene product obtainable, for example, through alternative splicing, DNA methylation, etc.

As used herein, the term "population" means a genetically heterogeneous collection of plants sharing a common genetic derivation.

As used herein, the term "progeny" refers to the descendant(s) of a particular cross. Typically, progeny result from breeding of two individuals, although some species (particularly some plants and hermaphroditic animals) can be selfed (i.e. the same plant acts as the donor of both male and female gametes). The descendant(s) can be, for example, of the F1, the F2, or any subsequent generation.

The term "QTL" is used herein in its art-recognized meaning.

The term "recipient pepper plant" is used herein to indicate a pepper plant that is to receive DNA or genomic introgression obtained from a donor pepper plant that comprises a genetic determinant responsible for increased fruit firmness.

The term "natural genetic background" is used herein to indicate the original genetic background of a QTL. Such a background may for instance be the genome of a wild accession of pepper.

As used herein, the phrases "sexually crossed" and "sexual reproduction" in the context of the presently disclosed subject matter refers to the fusion of gametes to produce progeny (e.g. by fertilization, such as to produce seed by pollination in plants). A "sexual cross" or "cross-fertilization" is in some embodiments fertilization of one individual by another (e.g. cross-pollination in plants). The term "selfing" refers in some embodiments to the production of seed by self-fertilization or self-pollination i.e. pollen and ovule are from the same plant.

As used herein, the term "pepper" means any plant, line or population formerly known under the genus name *Capsicum annuum*.

"Trait" is understood within the scope of the invention to refer to a characteristic or phenotype, for example increased fruit firmness. A trait may be inherited in a dominant or recessive manner, or may be monogenic or polygenic.

"Monogenic" is understood within the scope of the invention to refer to being determined by a single locus.

"Polygenic" is understood within the scope of the invention to refer to being determined by more than one locus.

"Dominant" is understood within the scope of the invention to refer to an allele which determines the phenotype when present in the heterozygous or homozygous state.

A "recessive" allele is only displayed when present in the homozygous state.

"Isogenic" is understood within the scope of the invention to refer to cultivated plants which are genetically identical, except that they may differ by the presence or absence of a heterologous or specific DNA sequence or specific genetic determinant.

"Harvesting stage" is understood within the scope of the invention to mean the date of harvesting ie the date the pepper fruit is removed from the plant.

"Immature Green stage" is defined as when the fruits are unripe and still growing in size. This stage is understood to be the first stage in the ripening process.

"Mature green stage" is defined as when the fruit is fully expanded mature, but unripe and follows the "immature green stage" in the ripening process. Traditionally, peppers harvested at the mature green stage are best suited for the commercial fresh market because they tolerate rough handling better than the riper stages and hold their shape the longest in storage, shipping, and on the supermarket shelf; however they somehow lack full aroma and taste.

"Breaker stage" is defined as first sign of red colour in the fruit, typically it occurs within 24 hours of the mature green stage. Peppers that are harvested at the "Breaker stage" usually have better flavor and taste but control pepper fruits have reduced firmness and are slightly less suitable for handling, packaging and transportation than peppers at the mature green stage or pepper according to the invention.

"Red ripe stage" or "ripe stage" is defined as when the fruits are fully red, or any other colour corresponding to ripe stage, with no sign of green colour.

"Genetic determinant" is understood within the scope of the invention to mean a gene or a locus in the genome or part thereof that is capable of contributing to the firmness of the fruits of the plant by influencing expression of the firmness trait at the level of the DNA itself, at the level of translation, transcription and/or activation of a final polypeptide product, i.e., to regulate metabolism in pepper fruit flesh leading to the phenotypic expression of the genotype. A genetic determinant is inheritable, ie it can be transferred to progeny by crossing.

"Commercially desirable characteristics" are understood within the scope of the invention to include but not be limited to superior fruit quality, disease resistance, insect resistance, uniform shape and size.

"Harvesting slot" is understood within the scope of the invention to mean the period of time from the harvesting stage until when the fruit is too ripe to be harvested for the purposes of commercial sale. Typically, the harvesting slot starts at mature green stage and continues until the breaker stage plus two to five days, depending on the cultivar and environmental conditions.

"Donor pepper plant" is understood within the scope of the invention to mean the pepper plant which provides the genetic determinant associated to significantly increased fruit firmness.

"Increase in fruit firmness" and "increased fruit firmness" are understood within the scope of the invention to mean pepper fruit which has lower maximum deformation value (for example as described in Example 1), statistically significant at $P<0.05$ or $P<0.01$ compared to fruit from a control plant.

"Control pepper plant" is understood within the scope of the invention to mean a pepper plant that has the same genetic background as the cultivated pepper plant of the present invention wherein the control plant does not have the genetic determinant—or part thereof—of the present invention associated to increased fruit firmness. A sibling plant without the genetic determinant associated with the trait of the present invention may be a control plant. In particular a control pepper plant is a pepper plant belonging to the same plant variety and does not comprise the genetic determinant. The control pepper plant is grown for the same length of time and under the same conditions as the cultivated pepper plant of the present invention. Plant variety is herein understood according to definition of UPOV. Thus a control pepper plant may be an inbred line or a hybrid provided that they have the same genetic background as the pepper plant of the present invention except the control plant does not have any of the genetic determinant of the present invention associated to increased fruit firmness.

"Anthesis" is understood within the scope of the invention to mean the period during which the flower is fully open and pollen is released.

"Processed food" is understood within the scope of the invention to mean food which has been altered from its natural state. Methods used for processing food include but are not limited to canning, freezing, refrigeration, dehydration and aseptic processing.

"Fresh cut market" is understood within the scope of the invention to mean vegetables on the market which have been minimally processed.

Differences between varieties or types of pepper are also observed with some varieties or types growing and producing mature fruits faster than other. In general, the time span from seeds sowing to first fruit setting varies between approximately 7 and 10 weeks, while the time span between first fruit setting and first fruit with full coloring varies between approximately 6 and 8 week. In glasshouse in the Netherlands, a pepper plant typically bears about 60 to 70 fruits over a period of 30 weeks. Pepper plants are grown in the open field or in glasshouse, with a harvest period of approximately 2 months in open fields, and of approximately 7 months in glasshouse.

Once harvested, the fruits are usually brought to a packing station where they may be stored briefly (around one day), preferably at cool temperature (e. g. at about 8-14° C.). The fruits are then transported to a retailer, for example a supermarket, generally in a cooled truck. The transport may take 2-3 days. In the supermarket, the fruits are placed on the shelves for about 1-2 days at a temperature of about 17-18 C. It takes therefore about 5-10 days from the field to consumers, who expect to be able to keep fruits with good appearance for a few more days.

The pepper plants of the present invention are capable of producing fruits exhibiting extended storability on the plant after complete ripe. Such fruits are capable of maintaining marketable quality for extended periods of time when fruits are kept on the plant and not harvested.

In another embodiment, the fruits of the plants of the present invention do not show delayed ripening. Fruits of plants of the present invention mature within time frames comparable to those of control plants, although slight differences may be observed depending for example on the growth conditions or on the genetic background of the plants examined. In particular, pepper plants of the instant invention set fruit and get full coloring around the same time as standard pepper plants. Absence of delayed fruit ripening is of advantage, as it does not delay the harvest of the first mature fruits.

In another embodiment, fruits of a pepper plant of the present invention exhibit outstanding post-harvest storability. In one embodiment, pepper fruits of the present invention remain firm for about 16 to about 24 days post-harvest, in one embodiment for about 18 to about 22 days post-harvest, when stored at a temperature of about 16 to about 18 C.

In one embodiment, the trait of the present invention is obtainable from pepper plant *Capsicum annuum* A13-1517-6 grown from seeds deposited with NCIMB, Aberdeen AB21 9YA, Scotland, UK on Feb. 5, 2015 under accession number NCIMB 42356 or from a progeny of said plant comprising said trait.

Accordingly, based on the description of the present invention, the skilled person in possession of pepper *Capsicum annuum* A13-1517-6 grown from seeds deposited with NCIMB, Aberdeen AB21 9YA, Scotland, UK on Feb. 5, 2015 under accession number NCIMB 42356 has no difficulty transferring the trait of increased fruit firmness of the present invention, ie the genetic determinant directing such a trait, to other pepper plants of various types using breeding techniques well-known in the art. The trait of the present invention is for example transferred to pepper plants producing fruit of various types or shapes, such as bell peppers or sweet peppers, big rectangular peppers, conical peppers, including long conical peppers, or blocky-type peppers and of various mature colors, such as red, yellow, orange or ivory.

In one embodiment, the present invention discloses a pepper plant obtainable by any one of the methods above, wherein the plant is capable of producing a fruit as described herein.

In one embodiment, the genetic information determining the trait of increased fruit firmness at harvesting stage according to the instant invention comprises a genetic determinant that is on a locus that is obtainable from pepper plant *Capsicum annuum* A13-1517-6 grown from seeds deposited with NCIMB, Aberdeen AB21 9YA, Scotland, UK on Feb. 5, 2015 under accession number NCIMB 42356, or from a progeny thereof.

Traits, in particular traits with a phenotype that can be scored, such as a resistance to a particular condition, can be followed genetically through crosses and the segregation of the trait can be scored in the progeny resulting from the cross. This allows, for example, one to determine whether a trait is dominant, recessive, or partially dominant. This also allows one to test whether genes determining a trait are at the same locus or at different associated or unassociated loci. This also allows one to test whether a trait is monogenic or polygenic.

Other crossing strategies are also used, e. g. with other combinations of homozygous or heterozygous plants, or with plants not comprising the trait. Segregation of the trait in the progeny is then scored. These crossing strategies and their corresponding segregation ratios are well known to the person skilled in the art, who also knows how to obtain and use appropriate "tester" plants, and how to interpret segregation ratios obtained from such crosses.

In another embodiment, the crossing schemes illustrated above are applied to the trait of the instant invention.

Commercial peppers are generally hybrids produced from the cross of two parental lines (inbreds). The development of hybrids requires, in general, the development of homozygous inbred lines (homozygous for almost 100% of the locus even if a few percent of the locus is heterozygous, ie not fixed), the crossing of these lines, and the evaluation of the crosses.

Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1 to F2; F3 to F4; F4 to F5, etc.

A single cross hybrid results from the cross of two inbred lines, each of which has a genotype that complements the genotype of the other. The hybrid progeny of the first generation is designated F1. In the development of commercial hybrids only the F1 hybrid plants are sought. Preferred F1 hybrids are more vigorous than their inbred parents. This hybrid vigor, or heterosis, can be manifested in many polygenic traits, including increased vegetative growth and increased yield.

Breeding in peppers can be accelerated by the use of double haploids obtained by another culture. Such a technique gives the possibility to secure the process by producing pure lines in a shorter period of time than the regular pedigree breeding process.

Plants within the *Capsicum annuum* species can be easily cross-pollinated. A trait is also readily transferred from one pepper plant to another plant, including pepper plants of different types using conventional breeding techniques, for example to further obtain commercial lines. The introgression of a trait into the elite line is for example achieved by recurrent selection breeding, for example by backcrossing. In this case, the elite line (recurrent parent) is first crossed to a donor inbred (the non-recurrent parent) that carries the trait. The progeny of this cross is then mated back to the recurrent parent followed by selection in the resultant progeny for the trait. After three, preferably four, more preferably five or more generations of backcrosses with the recurrent parent with selection for the trait, the progeny is heterozygous for the locus harboring the resistance, but is like the recurrent parent for most or almost all other genes The present invention offers the possibility for a grower to harvest less often a higher fruit quantity per plant or per surface area. This allows for a better planning of the harvest, a better planning of labor, a better efficiency of the harvest and more ripe fruits per harvest, while keeping the same fruit quality. A better efficiency and flexibility in the production of pepper fruit is possible.

The following examples are intended to provide illustrations of the application of the present invention. The following examples are not intended to completely define or otherwise limit the scope of the invention.

FIGURES

FIG. 1: Fruits of pepper plants identified in a plot with extra hard texture, cracked and that do not ripe. A, view from top. B, view from below. Fruits of plants homozygous for the trait, herein called Rocky plant (rr)

Figure 2:
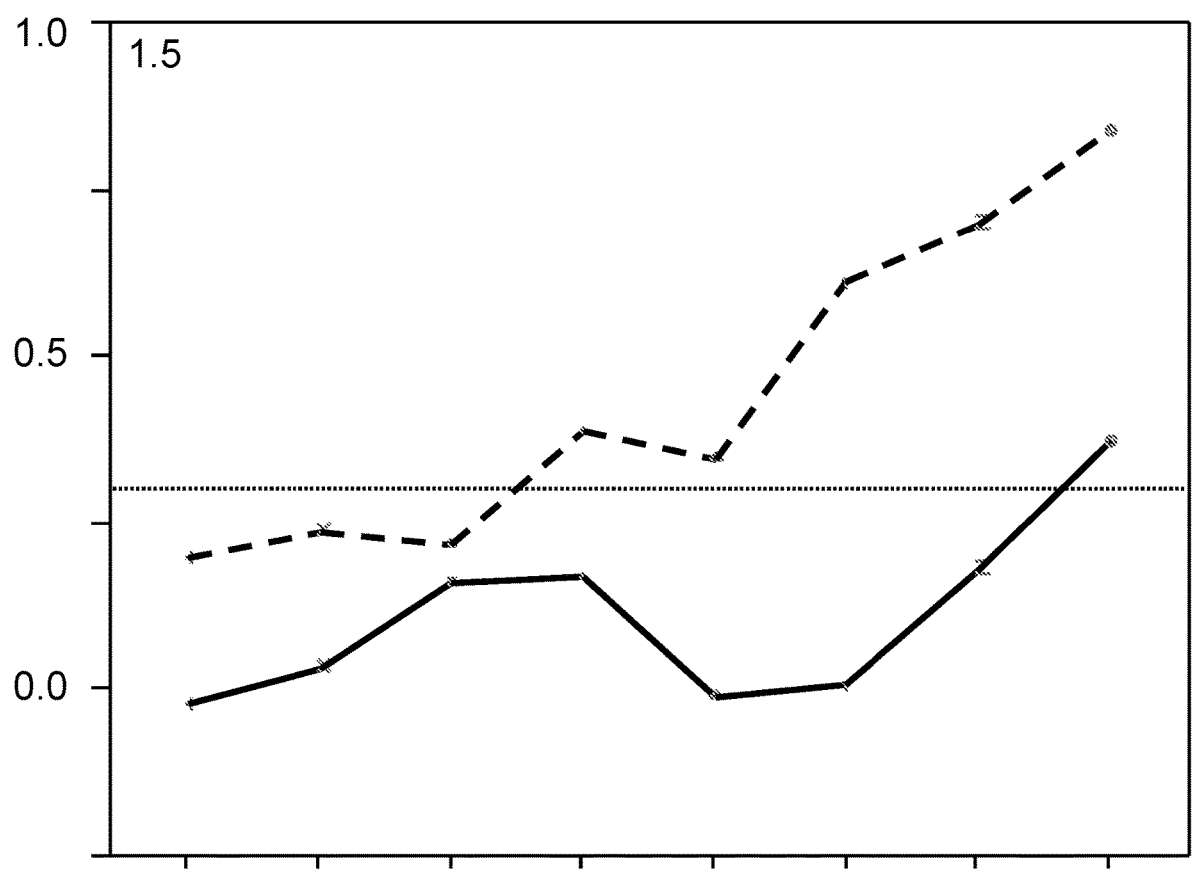

FIG. 2: Evolution of the firmness expressed as softness (mm deformation) of the fruits following anthesis for wild type fruits (RR) (dotted line) and fruits according to the invention that are heterozygous for the genetic determinant (rR) (continuous line).

Figure 3:
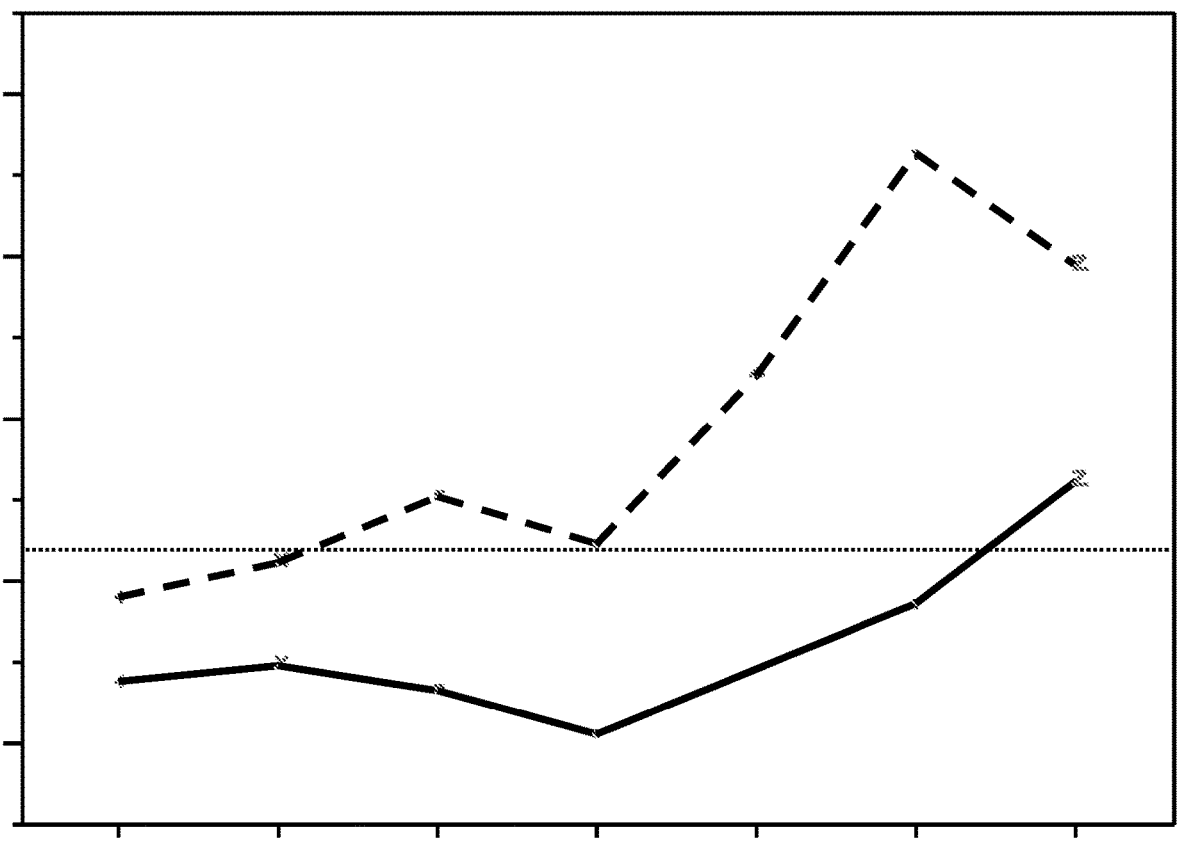

FIG. 3: Evolution of the firmness expressed as softness (mm deformation) of the fruits following breaker for wild type fruits (dotted line) and fruits according to the invention that are heterozygous for the genetic determinant (rR) (continuous line).

Figure 4:
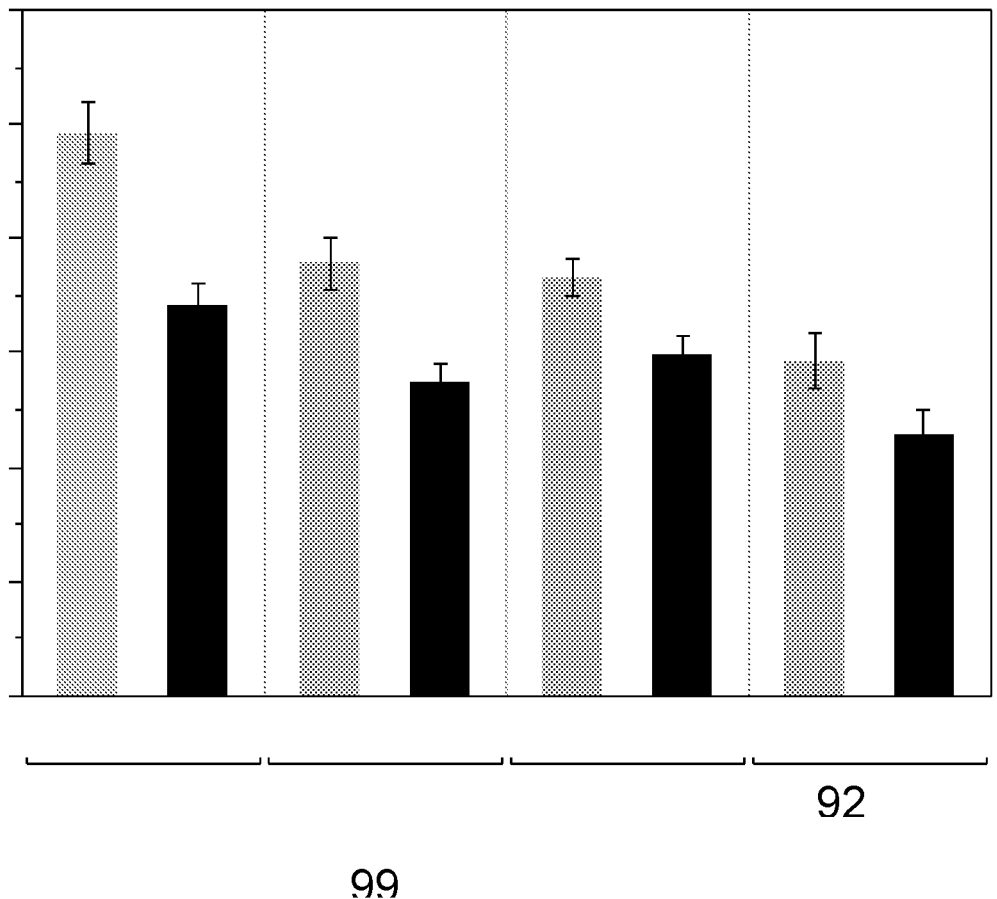

FIG. 4: Number of days from anthesis to harvest for different harvesting date for the normal wild type pepper plant (N) and for heterozygous plant for the genetic determinant according to the invention (het, rR)).

Figure 5:
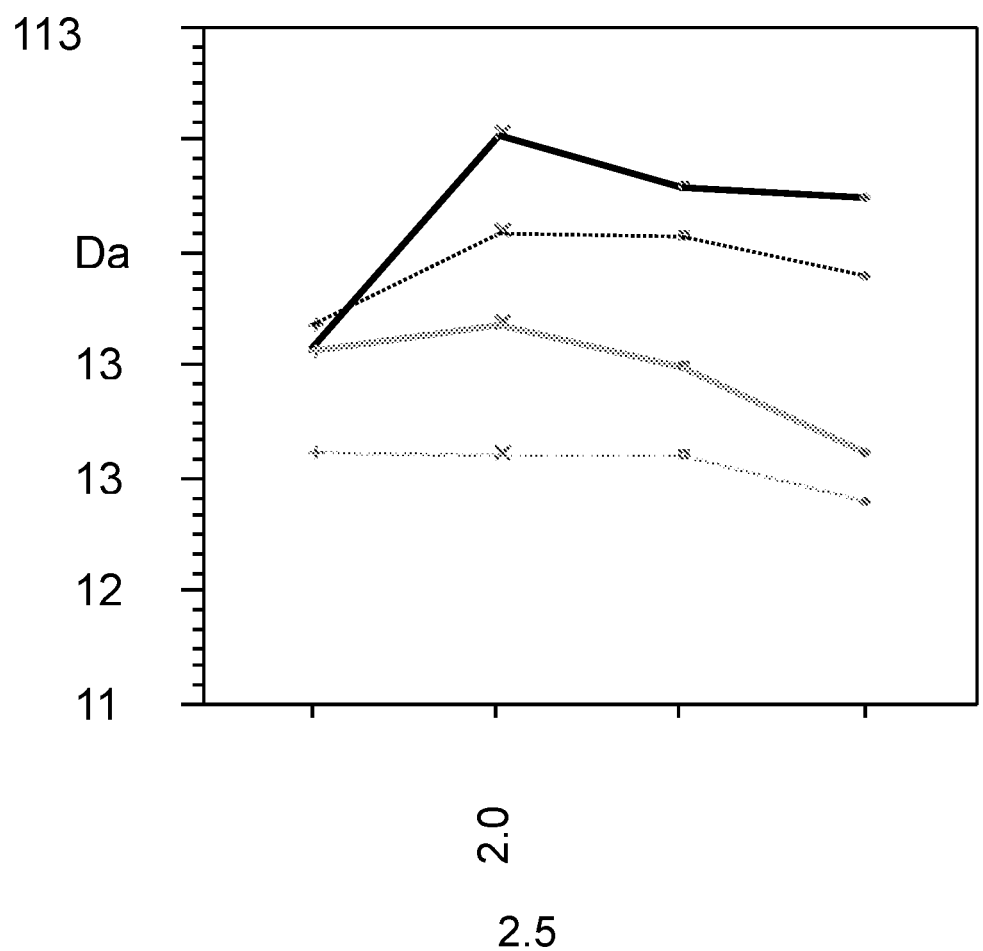

FIG. 5: Fruit weight for the normal wild type pepper plant (RR) (in grey) at harvest (continuous grey line) and after 21 days storage at 8° C. (dotted grey line) and for heterozygous plant (rR) (in black) for the genetic determinant according to the invention, at harvest (continuous black line) and after 21 days storage at 8° C. (dotted black line).

EXAMPLES

Growth and Cultivation Conditions

Pepper plants were grown at Netiv HaHasara for two growing seasons, i.e., spring and summer; and fall and winter the following year. As in most plants, especially peppers, the described characteristics are related to growth, seasons and conditions. The following example is presented: Netiv Haasara conditions: unheated plastic covered greenhouse, covered by shading net (40%, from May); sandy soil; sowing in February; 2,500 plants per 1,000 m2; Spanish-style side support cane; non-pruning of fruits and plants, as in accepted commercial practice.

In F2 population of a hybrid variety used in field trials, was identified a non-ripening plant, likely a mutant, that had green hard and cracked fruits, while the rest of the plants in the population were colored and normal ripening. Such a plant is designated as "Rocky" in the remaining part of the experimental section and refers to plant according to the invention, i.e. exhibiting high firmness compared to other plants, not mutated. The fruits stood out being very firm, crunchy more than a regular pepper. The taste was not attractive, and did not resemble neither ripe nor mature-green pepper fruits. Because of its extra hard firmness those fruits were retained as they it could have some useful potential in breeding.

On the vine, the fruits of that mutant plant do not ripe, do not change color, do not become sweet and do become cracked. For the isogonic siblings (wt) fruits at the same age do ripe, the texture of mutant becomes more and more firm with increase in turgor pressure leading to extremely firm fruits.

Rescue and Propagation

Fruits were harvested and seeds extracted, and immediately sent to the nursery in order to use them in crosses, and see their hybrids in the next season. However the seeds completely failed to germinate and needed embryo rescue to germinate and grow into a plant. As a last resort, the non-ripening mutant plants was pulled out from the greenhouse and replanted and used as male parent to produce various hybrids thru crosses with pepper lines.

F2 populations from the hybrids with the non-ripening plant were grown in the following years. The ratio of non-ripening plants in those populations, fitted a single recessive mutant, with frequency of 0.25. In the F2 population that appeared somewhat more firm, and many of them segregated again as a single gene. The work was continued in order to maintain it and as an easy way to develop isogenic lines for further study. At that time, the notion that heterozygous plants are firmer and normal ripening was established. In one case 20 families of heterozygous plants on a total of 536 plants gave 75.1%:24.9% following 3:1 ripening to non-ripening in F2.

The near isogenic lines were developed by continues propagation of plants heterozygous for the genetic determinant. Each generation the resemblance increased in 50%. The heterozygous plants were derived from the rescue population described herein. Developing plants near isogenic heterozygous was done by crossing the wild type plant as female with homozygous isogenic as male. This allowed to develop Normal plants isogenic to the heterozygous plant according to the invention.

Plant Material

Genetic lines: In this study we developed and used four different lines: F8-47 red, F8-49 red and F8-48 yellow, which were derived from a common parent in the F4 generation and the line I8-7043 yellow, derived from a different genetic background. The isogenic lines were generated by continuous selfing of individual plants heterozygous for the mutation. In order to isolate Rocky and normal isogenic homozygote lines we collected fruits from plants with ripe fruits (i.e. fruits from all the non-rocky plants in the plot) derived from a single plant heterozygote to the Rocky mutation. Next we examined its individual offspring plants by a progeny test, 20-25 plants per plot of each offspring plant. Parents that yielded 100% progeny plants producing normal fruits were classified and used as a normal homozygote lines. Parent plants that produced segregating populations (i.e. at least 1 Rocky plant per plot) were used to obtain Rocky plants as well as to advance the isogenic normal material.

Plant growth: Most of the pepper fruits used for experiments in this study was grown in a commercial greenhouse at Tzofar, mid Arava desert area, during the winter season (mid-August to April) under regular local growing conditions. Summer fruits were grown at Hatzav, in the coastal plain of Israel, under regular growing conditions (May to September). In a few cases the fruits were obtained from plants grown at the faculty greenhouse under constant conditions of 25° C. and natural day light.

Fruits marking: fruits for experiments were marked weekly; at diameter of ~10 mm. Fruit at this stage are estimated to be 5-7 days after anthesis.

Deposit: Seeds of hybrid pepper plant *Capsicum annuum* A13-1517-6 have been deposited with NCIMB, Aberdeen AB21 9YA, Scotland, UK on Feb. 5, 2015 under accession number NCIMB 42356.

Firmness Measurement

Pepper fruits firmness was measured by a modified Cornell firmness tester (Hamson, 1952). In this method, fruit firmness is measured as the extent of fruit deformation resulting from loading 1 kg weight for 10 seconds. To avoid negative values given by the device, the absolute measured fruit deformation was defined as "fruit softness" (mm). Thus, softer fruits exhibit higher values while firmer fruits show lower values. For measuring fruits softness during ripening we used the mean softness of 4-10 fruits from each ripening stage.

The instrument was designed according to the instrument used by (Ben- Yehoshua, S., Shapiro, B., Chen, J. and Lurie, S. (1983). Mode of action of plastic film in extending life of lemon and bell pepper fruits by alleviation of water stress. Plant Physiology 73: 87-93) for measuring peppers. It is based on a static loud with a weight (1 Kg) and measuring the distance of deformation after 10 seconds. The machine is equipped with digital distance measurement and linker to a computer.

Embryo Rescue

Seeds are removed from mutant fruits (homozygous) at advanced stage 60-90 days after anthesis, when its normal sibling is ripe. Seeds for propagation are removed from the fruit and used immediately. Seeds are soaked in 1% sodium-Hypochlorite for 5-10 minutes and washed for 30 minutes in running tap water.

Embryo Extraction

Under a binocular the seed coat is easily cut by scalpel at the wide end of the seed, and the embryo is simply pulled out by thin tweezers, and transferred to modified medium given bellow in petri dishes. Plates are placed at 25° C. and 12 hours day length in culture room under fluorescent light.

Hardening

Within a week small seedlings with two cotyledons appear, and moved to JIFFY and moved to a growth chamber with high humidity (75% RH). After a few days they are moved to green house to complete growth and to be planted in a greenhouse.

Embryo Rescue Medium

The basal nutrient medium (BM) (sigma M5524) contained Murashige and Skoog salts and organic components and vitamin powder (sigma M7150). The embryo induction medium consisted of BM supplemented with 3% sucrose (S7903), 10 µM thidiazuron (TDZ) (sigma P6186), 0.25% phytagel (sigma P8169), 2 mg/L BA (6_benzyl-aminopurine) (sigma B-6750) and 0.3% charcoal activated (C-3790). The pH of the medium was adjusted to 5.8 prior to autoclaving.

RESULTS

1. "Rocky" is a Recessive Single Locus Mutation

While normal fruits (genotype designated in this study as RR) ripen and change their color, the fruits of Rocky (rr) plants stay green, become firmer and tend to crack. At this stage the two phenotypes are clearly distinct. The phenotypes of the progenies of 20 self pollinated heterozygous (Rr) parents of different genetic backgrounds were determined in the years 2008-2011. The overall ratio of the Rocky (rr) plants to the normally ripening plants (either homozygotes (RR)) or heterozygotes (Rr) is 141 (24.9%) to 433 (75.1%) respectively. In $\chi 2$ test (H0: Rocky relative portion=0.25, non-rocky relative portion=0.75) H0 was accepted at 99% significance ($p(\chi 2)>0.94$). These results indicate that Rocky is a recessive mutation controlled by a single locus and that Rocky plants are homozygous recessive for the mutation (rr).

2. Firmness

On FIG. 2 it can be seen that the firmness of the fruits of the plants according to the present invention exhibit a low deformation all along the period post anthesis till harvest compared to a sibling isogenic plant but without the genetic determinant for the trait of the present invention.

On FIG. 3 it can be seen that the firmness during the breaker period is also increased for the pepper fruit of the invention compared to fruits of sibling isogenic plants without the genetic determinant for the trait of the present invention.

From FIG. 4 it can be seen that the duration of the period during which the fruit can be kept on the plant, the period from anthesis to harvest is longer for the fruits of the plants according to the invention that are heterozygous for the genetic determinant of the present invention compared to sibling isogenic plants without the genetic determinant. Also, the fruit weight at harvest and after storage is higher for the longer for the fruits of the plants according to the invention that are heterozygous for the genetic determinant of the present invention compared to sibling isogenic plants without the genetic determinant.

3. Reciprocal Hybrids Between Rocky and Normal Plants

Fruits resulting from reciprocal crosses between normal and Rocky plants were examined in two different lines (18-7043 and F8-49). In both cases, when Rocky female parents (genotype rr homozygous for the trait/locus according to the present invention) were pollinated with either Rocky (rr) or normal (RR, not carrying the trait/locus according to the present invention) pollen, the phenotypes of the fruits (rR or rr; i.e. heterozygous or homozygous for the trait/locus of the present invention) and seeds which developed were identical to the Rocky homozygotes phenotype (firm fruits, large seeds, developmentally delayed embryos and lack of an endosperm). When normal female parents (RR, not carrying the trait/locus according to the present invention) were fertilized with either Rocky (rr) or normal pollen (RR), the phenotype of the fruits and seeds appeared normal. However, the heterozygous plants (Rr) were exhibiting a fruit phenotype with enhanced firmness and capable of normal ripening as compared to the normal (RR) plants not carrying the locus of the invention. Such plants are still with the scope of the invention. The results show that the phenotypes of the fruits and seeds of first generation crosses are determined by the genotype of the maternal plant. However, the selfing of this progeny can give rise to plants having fruit with Rocky phenotype.

The invention claimed is:

1. A hybrid pepper *Capsicum annuum* A13-1517-6 grown from seeds deposited with NCIMB, Aberdeen AB21 9YA, Scotland, UK on Feb. 5, 2015 under accession number CIMB 42356.

2. A pepper plant which produces fruits with significantly increased fruit firmness at the harvesting stage,
wherein said increased fruit firmness is controlled by a genetic determinant,
wherein said increased fruit firmness is defined as a fruit deformation under a 1 kg load force that is lower than that of a fruit from a control pepper plant which does not have the said genetic determinant
wherein said genetic determinant is a monogenic recessive gene mutation present in the pepper plant seed deposit made under accession number NCIMB 42356, and
wherein said pepper plant is produced by introgression of the genetic determinant from a donor pepper plant into a recipient pepper plant by crossing the donor pepper plant and recipient pepper plant and selecting plants which grow fruits with increased fruit firmness, wherein the donor plant is the pepper plant of claim 1.

3. The pepper plant according to claim 2, characterized in that the pepper fruit deformation represents 50% to 95% of that of a fruit from a control pepper plant which does not have the said genetic determinant.

4. The pepper plant according to claim 2, characterized in that the pepper fruit deformation represents 50% to 80% of that of a fruit from a control pepper plant which does not have the said genetic determinant.

5. The pepper plant according to claim 2, characterized in that the pepper fruit deformation represents 50% to 70% of that of a fruit from a control pepper plant which does not have the said genetic determinant.

6. The pepper plant according to claim 2, characterized in that the genetic determinant is homozygous or heterozygous.

7. An agronomic method of producing pepper plant producing pepper fruits with increased fruit firmness comprising the steps of:
i) providing a pepper plant according to claim 2;
ii) multiplicating/propagating said pepper plant
iii) allowing the plant to grow pepper fruits with increased fruit firmness; and
iv) harvesting said pepper fruits.

8. A method for producing a pepper plant producing fruits with increased fruit firmness, comprising the steps of:
  i) providing seeds of a pepper plant according to claim 2;
  ii) germinating said seed and growing a mature, fertile plant therefrom;
  iii) inducing self-pollination of said plant grown under (ii), growing fruits and harvesting the fertile seeds therefrom, and
  iv) growing plants from the seeds harvested under iii) and selecting plants which grow fruits with increased fruit firmness.

9. The method according to claim 8, characterized in that the seeds of the pepper plant are from a hybrid pepper plant of *Capsicum annuum* A13-1517-6 grown from seeds deposited with NCIMB, Aberdeen AB21 9YA, Scotland, UK on Feb. 5, 2015 under accession number NCIMB 42356.

10. A method of producing a pepper plant producing fruits with increased fruit firmness comprising the steps of
  i) providing seeds of a pepper plant according to claim 2;
  ii) germinating said seed and growing a mature, fertile plant therefrom;
  iii) crossing the plant obtained in ii) with a pepper plant which does not have the trait of increased fruit firmness, growing fruits and harvesting the fertile seeds therefrom and
  iv) growing plants from the seeds harvested under iii) and selecting plants which grow fruits with increased firm firmness.

11. A method for expanding the harvesting slot of pepper fruits, which comprises growing the pepper plant according to claim 2.

12. Plant material obtainable from a plant according to claim 2 wherein said plant material comprises the genetic determinant and is at least one of leaves, stems, roots, flowers or flower parts, fruits, pollen, egg cells, zygotes, seeds, cuttings, cell or tissue cultures, or any other part or product of the plant which still exhibits the increased fruit firmness phenotype according to the invention.

13. A seed of a pepper plant according to claim 2, wherein the seed comprises the genetic determinant.

14. The pepper plant according to claim 6, characterized in that the genetic determinant is heterozygous.

15. A pepper plant which produces fruits with significantly increased fruit firmness at the harvesting stage,
  wherein said increased fruit firmness is controlled by a genetic determinant,
  wherein said increased fruit firmness is defined as a fruit deformation under a 1 kg load force that is lower than that of a fruit from a control pepper plant which does not have the said genetic determinant
  wherein said genetic determinant is a monogenic recessive gene mutation present in the pepper plant seed deposit made under accession number NCIMB 42356, and
  wherein said pepper plant is produced by crossing the pepper plant of claim 8 with another pepper plant.

* * * * *